(12) United States Patent
Yoneda et al.

(10) Patent No.: US 7,631,999 B2
(45) Date of Patent: Dec. 15, 2009

(54) LINE LIGHT IRRADIATION DEVICE

(75) Inventors: Kenji Yoneda, Kyoto (JP); Takashi Sugita, Kyoto (JP)

(73) Assignee: CCS, Inc., Kyoto (JP)

( * ) Notice: Subject to any disclaimer, the term of this patent is extended or adjusted under 35 U.S.C. 154(b) by 59 days.

(21) Appl. No.: 10/567,234

(22) PCT Filed: Aug. 4, 2004

(86) PCT No.: PCT/JP2004/011157

§ 371 (c)(1),
(2), (4) Date: Feb. 3, 2006

(87) PCT Pub. No.: WO2005/015186

PCT Pub. Date: Feb. 17, 2005

(65) Prior Publication Data

US 2006/0215151 A1   Sep. 28, 2006

(30) Foreign Application Priority Data

Aug. 6, 2003  (JP) .............................. 2003-288283
Mar. 31, 2004 (JP) .............................. 2004-106654

(51) Int. Cl.
*G02B 6/04* (2006.01)

(52) U.S. Cl. ............... 362/554; 362/217.01; 362/217.1; 362/217.14; 362/225; 362/551; 356/237.1; 356/237.2; 356/237.3; 356/237.4; 356/237.5

(58) Field of Classification Search ............... 362/217, 362/225, 245, 551, 554, 555, 800, 217.01, 362/217.1, 217.11, 217.12, 217.14, 217.15, 362/217.16; 356/237.1, 237.2, 237.6, 237.3, 356/237.4, 237.5, 239.2

See application file for complete search history.

(56) References Cited

U.S. PATENT DOCUMENTS 5,148,303 A * 9/1992 Biard .......................... 398/113
5,185,638 A * 2/1993 Conzola et al. .......... 356/237.2
5,222,794 A * 6/1993 Windross ..................... 362/554

(Continued)

FOREIGN PATENT DOCUMENTS

DE         102 56 365         7/2003

(Continued)

*Primary Examiner*—Sharon E Payne
*Assistant Examiner*—Mary Zettl

(57) ABSTRACT

In order to provide a line light irradiation device that can improve efficiency of condensing light with a compact size and that is almost free from unevenness of lighting, the line light irradiation device of the present claimed invention comprises multiple light emitting parts 2 each of which is provided with a light irradiating part 21 where multiple optical fibers 4 are thickly arranged in a line with light leading out end portions 4a of the multiple optical fibers 4 forming a straight line and a columnar lens 22 arranged to extend along a direction of the line P in front of the light irradiating part 21 in pairs, and that irradiate line light LL that converges into a straight line, and a holding body 3 that is arranged to face to a work W as being an object on which the line light LL is to be irradiated, on which monitoring bores 3a, 3b are arranged to penetrate in order to monitor the work W, and that holds the light emitting parts 2 so that each optical axis face of the line light LL irradiated from each of the light emitting parts 2 crosses on a predetermined straight line.

15 Claims, 10 Drawing Sheets

U.S. PATENT DOCUMENTS

| | | | |
|---|---|---|---|
| 5,251,280 A * | 10/1993 | Asada et al. | 385/115 |
| 5,260,766 A * | 11/1993 | Armitage | 356/237.1 |
| 5,268,977 A * | 12/1993 | Miller | 385/33 |
| 5,432,600 A * | 7/1995 | Grollimund et al. | 356/237.2 |
| 5,596,409 A * | 1/1997 | Marcus et al. | 356/479 |
| 5,953,113 A * | 9/1999 | Poffenbarger | 356/73.1 |
| 6,757,058 B1 * | 6/2004 | Carman et al. | 356/237.2 |
| 6,782,337 B2 * | 8/2004 | Wack et al. | 702/155 |
| 2003/0147254 A1 | 8/2003 | Yoneda et al. | |
| 2003/0193817 A1 * | 10/2003 | Yoneda et al. | 362/555 |

FOREIGN PATENT DOCUMENTS

| | | |
|---|---|---|
| JP | 63-104872 | 5/1988 |
| JP | 10-021729 | 1/1998 |
| JP | 2002-221491 | 8/2002 |
| JP | 2003-202294 | 7/2003 |

* cited by examiner

LINE LIGHT IRRADIATION DEVICE

TECHNICAL FIELD

This invention relates to a lighting device for product inspection used for detecting flaws, recognizing a mark on a surface of a work or the like, more specifically a light irradiation device that irradiates line light.

BACKGROUND ART

Conventionally, various lighting devices (light irradiation device) have been developed to carry out an inspection of a surface of a work. For example, an annular-shaped lighting device that irradiates light of a low angle from its circumference, a line-shaped lighting device that irradiates line light on a work, or other lighting device that meets various aspects of a work or various purposes of irradiating light have been known as the lighting devices as shown in Japan Patent laid open 1.

Especially, a line-shaped lighting device of a converging type is so arranged that bullet-shaped LEDs are laid out in a line and a cylindrical lens is arranged in front of the bullet-shaped LEDs so as to irradiate thin line-shaped light on a work.

Japan Patent laid open 1 number: 10-21729

DISCLOSURE OF THE INVENTION

Problems to be Resolved by the Invention

However, the LEDs have a certain level of a light emitting area and can not be considered as a point light source. Then there is a problem that it is difficult to gather rays of light so that enough lighting luminous intensity can not be obtained if a lens whose focal distance is short is used with an attempt to, for example, downsizing. On the one hand, if a lens whose focal distance is long is used, it is possible to gather rays of light modestly. In this case, however, a size of the lens becomes extremely big, thereby to fail downsizing and being low in cost. Especially, if cylindrical lenses are arranged in multiple lines, a problem of a lens size becomes significant. As a result of this, an arrangement in which multiple lines of line light each of whose three-dimensional angle differs can be gathered and irradiated has been less known.

As mentioned above, since light focusing efficiency (light use efficiency) and downsizing are in a trade-off relationship for this type of a conventional line-shaped lighting device, an arrangement of the conventional line-shaped lighting device is low in design freedom and half-finished, resulting in difficulties to meet a requirement for lighting device. Furthermore, in case that multiple LEDs are laid out in a line, a gap is formed between an LED and its adjacent LED from a viewpoint as a lighting source even though the LEDs are arranged thickly. As a result, there is a problem that unevenness of lighting is generated along a direction of the line.

The present claimed invention intends to solve the above-mentioned problems and its main object is to provide a line light irradiation device that is compact and that can improve light focusing efficiency without substantial unevenness of lighting.

Means for Solving the Problems

More specifically, the line light irradiation device in accordance with this invention comprises multiple light emitting parts each of which is provided with a light irradiating part where multiple optical fibers are thickly arranged in a line or in multiple lines with light leading out end portions of the multiple optical fibers forming a straight line of a predetermined width and a columnar lens arranged to extend along a direction of the line in front of the light irradiating part in pairs, and that irradiate line light that converges into a straight line, and a holding body that is arranged to face to a work as being an object on which the line light is to be irradiated, on which a monitoring bore is arranged to penetrate in order to monitor the work, and that holds the light emitting parts so that each optical axis face of the line light irradiated from each of the light emitting parts crosses on a predetermined straight line.

"Thickly" here is a state that each of the light leading out end portions is arranged with almost no space therebetween.

In order to make it possible to irradiate light of mutually different three-dimensional angle, it is preferable that each light emitting part is arranged on the holding body so that the optical axis face of the line light irradiated from each light emitting part is arranged radially viewed from the direction of the line.

As a more preferable embodiment for uniform lighting, it is preferable that the line light from each light emitting part is arranged side-by-side with no space therebetween so as to be the line light of continuous three-dimensional angle. In order to do so, it is preferable that each columnar lens is arranged generally on a straight line viewed from the direction of the line.

In order to hold multiple light leading out portions in a group easily, it is preferable that the light irradiating part further comprises a pair of pinching plates and the pinching plates hold the light leading out end portions of the multiple optical fibers by pinching them.

As an arrangement to introduce light into each optical fiber effectively and uniformly, it is preferable that a binding part is formed by binding each light introducing end portion of the optical fibers and light from a light source is introduced into the binding part.

Although the optical fiber itself is of flexibility that can be bent, it is very difficult for a band of the optical fibers to inflect each optical fiber toward the direction of the line. As a result, if the band of the optical fibers is shaped to be, for example, axisymmetric to the center, the light sources have to be arranged lengthwise in case multiple light emitting parts are provided, thereby failing to be downsized in a direction toward thickness. With a view to solve this problem, in order to make it possible to mount the band of the optical fibers with ease even though multiple light sources are arranged along the direction of the line on the holding body and to be downsized in the direction toward the thickness, it is preferable that the binging part is located to deviate to either one of directions with respect to a center line of the light irradiating part.

As a concrete embodiment of the light source it is represented that the light source that introduces light into the optical fibers is a power LED that can continuously flow current greater than or equal to 200 mA.

In order to make it possible to change a width of the irradiated line light so that various aspects of the light can be irradiated, it is preferable that a distance between the light irradiating part and the columnar lens can be varied.

In order to make it possible to set a position where the light is converged on the work in connection with a change of a distance between the work and the light emitting part, it is preferable that the light emitting part is rotatably around a rotational axis that is parallel to the direction of the line and the rotational angle can be set.

In order to line up multiple types of the light irradiation devices that can irradiate line light whose length differs from each other with suppressing a cost increase by standardizing basic components, it is preferable that the multiple light irradiating parts are arranged serially along the direction of the line. This is because the length of the line light can be easily changed by changing a number of the serially arranged light irradiating parts.

Especially, in order to promote standardization of the basic components, it is preferable that each length of the light emitting part is identical (more preferably, the shape thereof is identical). On the contrary, with this arrangement, the length of the line light is limited to a length that is an integral multiplication of the length of the light irradiating part. In order to increase a number of variations of the length of the line light, it is preferable the light irradiating parts of several different lengths are serially arranged. In spite of this, if too many variations are set for the length of the light irradiating part, an effectiveness of standardizing components is reduced.

In order to make an effect of reducing a cost more remarkable by standardizing the columnar lens also, it is preferable that multiple light emitting parts of the identical length or of several different lengths are arranged serially.

In order to make it possible to reduce a burden on an image processing unit used in case of product inspection or to flexibly meet other user requirement with realizing various types of light irradiation such as intensity of illumination is changed for each part of the line light by making use of the above-mentioned arrangement, it is preferable that the light source is arranged for each of the light irradiating parts individually.

Advantageous Effect of the Invention

In accordance with the arrangement of this invention, since it is possible for the light irradiating part to irradiate extremely fine line-shaped light, the line light that converges into extremely fine line-shaped light can be obtained even though the light emitting part is downsized by arranging the columnar lens whose focal distance is short close to the light irradiating part. This arrangement makes it possible to provide varieties of light irradiating aspect by arranging multiple light emitting parts and to downsize each light irradiating part. In addition, it is possible to obtain the line light that ideally converges into a line-shape and that is efficient in light focusing. In addition, since each of the light introducing out end portions is arranged thickly, the line light is free from unevenness, thereby enabling the lighting device that is high in evenness.

BEST MODE FOR CARRING OUT THE INVENTION

Figure 1:
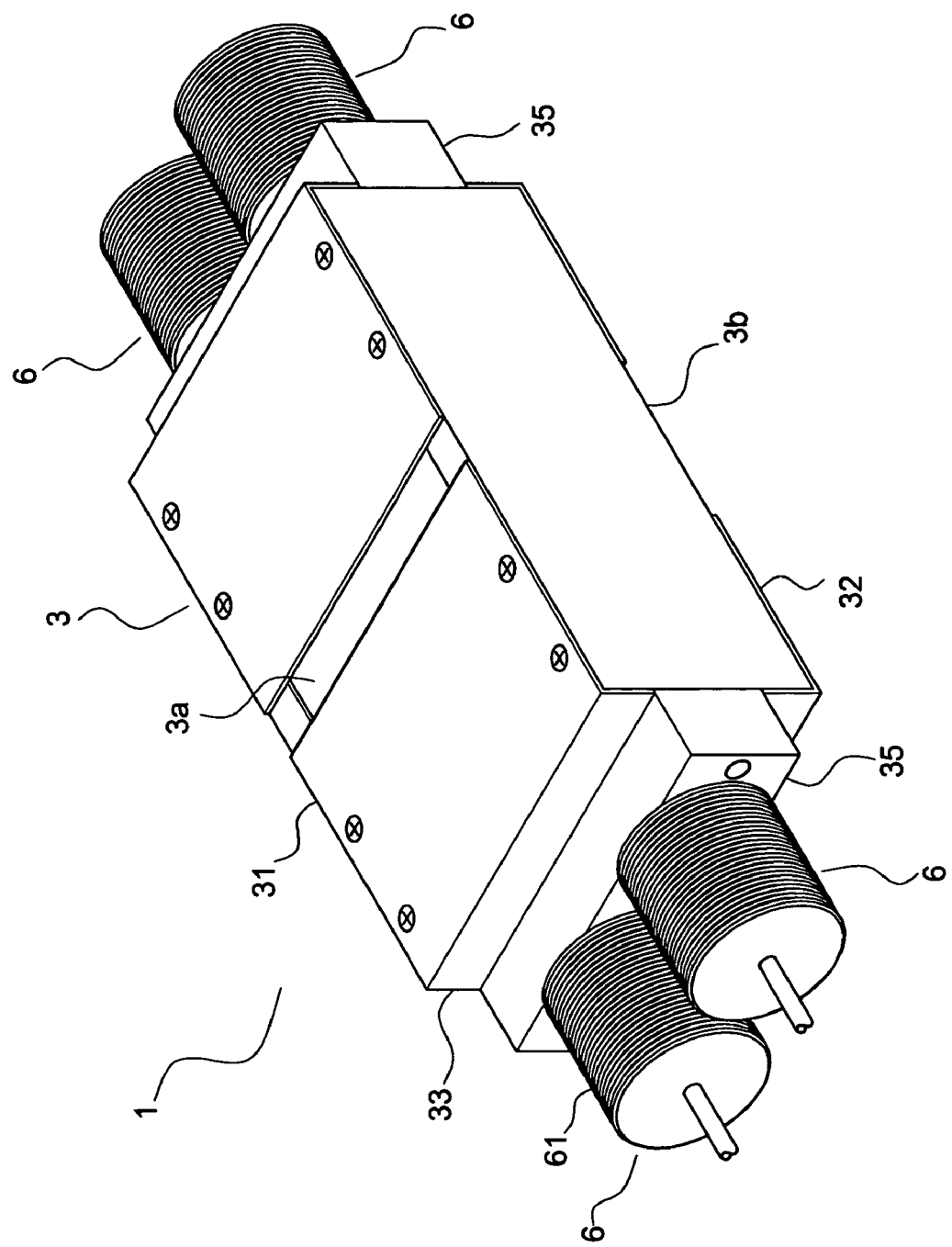
FIG. 1 is an overall perspective view of a line light irradiation device in accordance with one embodiment of the present claimed invention.
Figure 2:
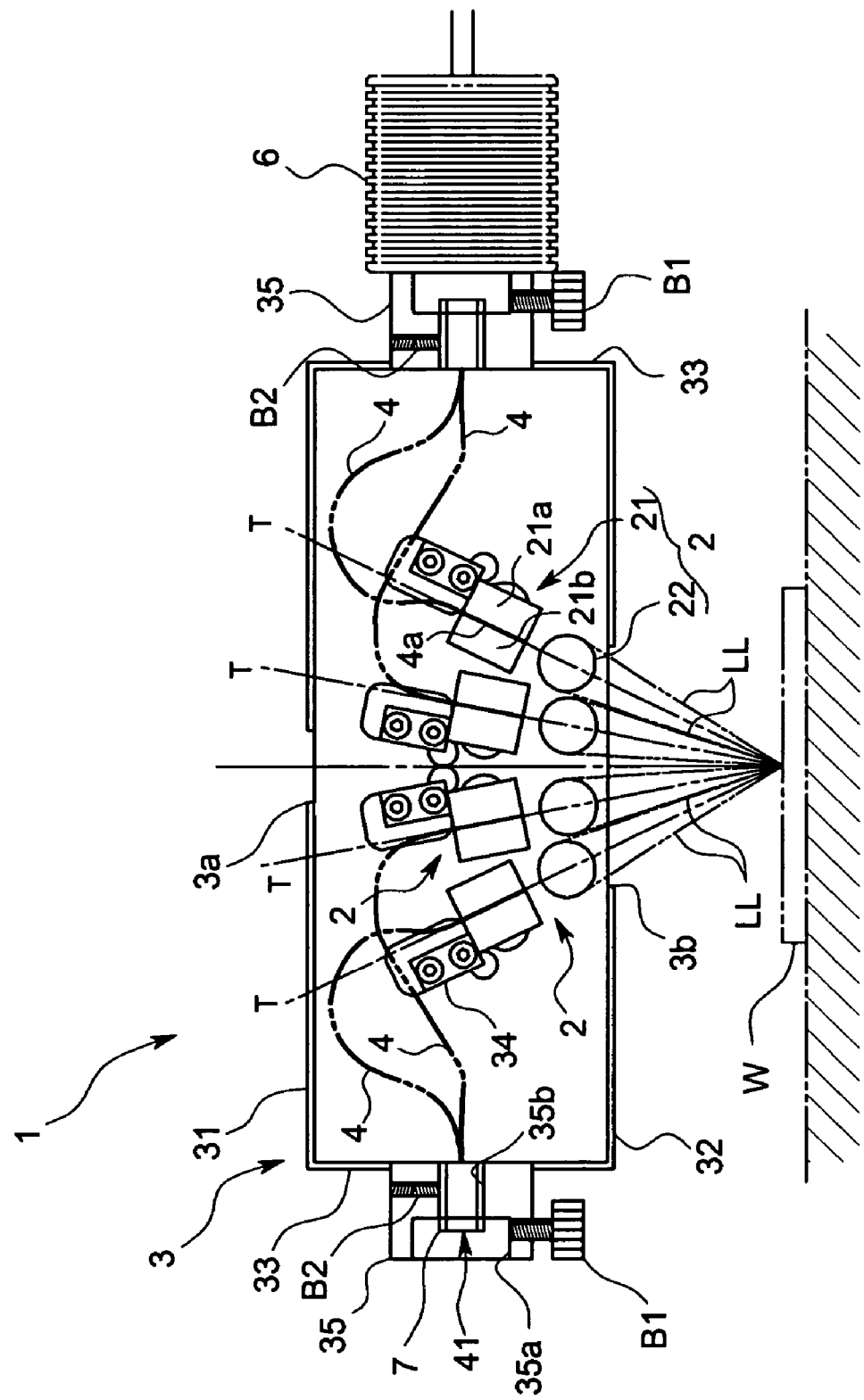
FIG. 2 is a general longitudinal cross-sectional view of the line light irradiation device in accordance with this embodiment.
Figure 3:
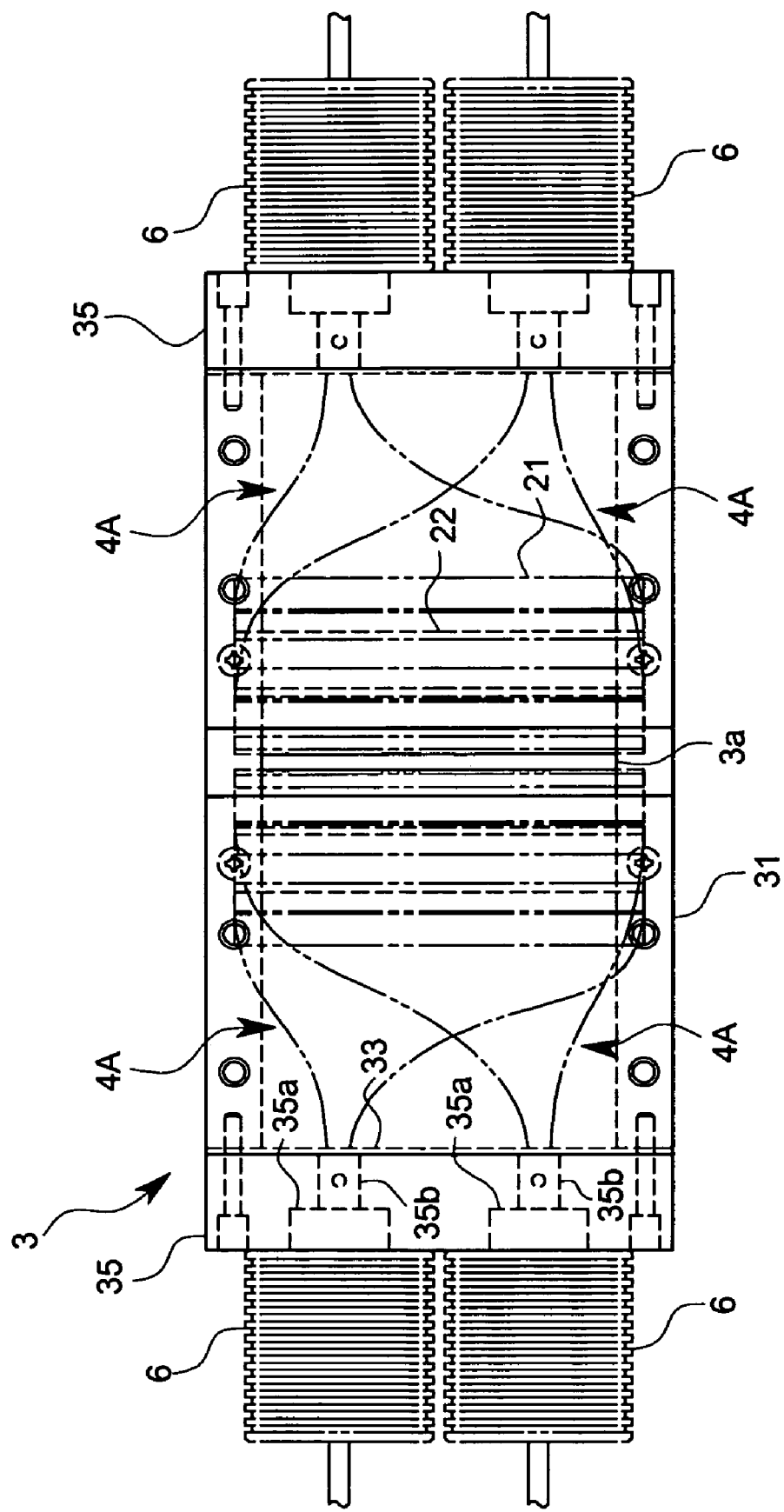
FIG. 3 is a plane view showing a casing in a state that a rod lens of the line light irradiation device in accordance with this embodiment is mounted.
Figure 4:
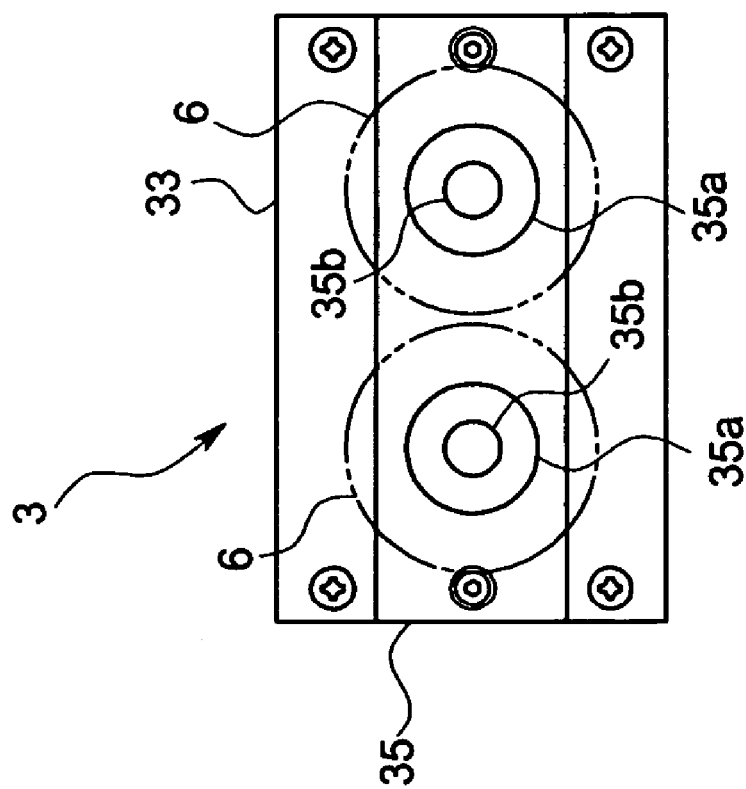
FIG. 4 is a side view of the casing in accordance with this embodiment.

One embodiment of the present claimed invention will be described in detail with reference to the accompanying drawings.

A line light irradiation device 1 in accordance with this embodiment comprises, as shown in FIG. 1 through FIG. 4, multiple light emitting parts 2 that irradiate line light LL converging in a line shape and a casing 3 as being a holding body that holds the light emitting parts 2.

Each of the light emitting parts 2 is provided with a light irradiating part 21 where extremely fine (diameter of 0.25 mm in this embodiment) multiple optical fibers 4 are thickly arranged in a line or in multiple lines with its light leading out end portion 4a arranged along a predetermined direction of the line P (shown in FIG. 5 and FIG. 6) and a rod lens 22 as being a columnar lens arranged to extend along the above-mentioned direction of the line P in front of the light irradiating part 21 in pairs. Multiple light emitting parts 2 are arranged radially viewed from the direction of the line P.

Figure 5:
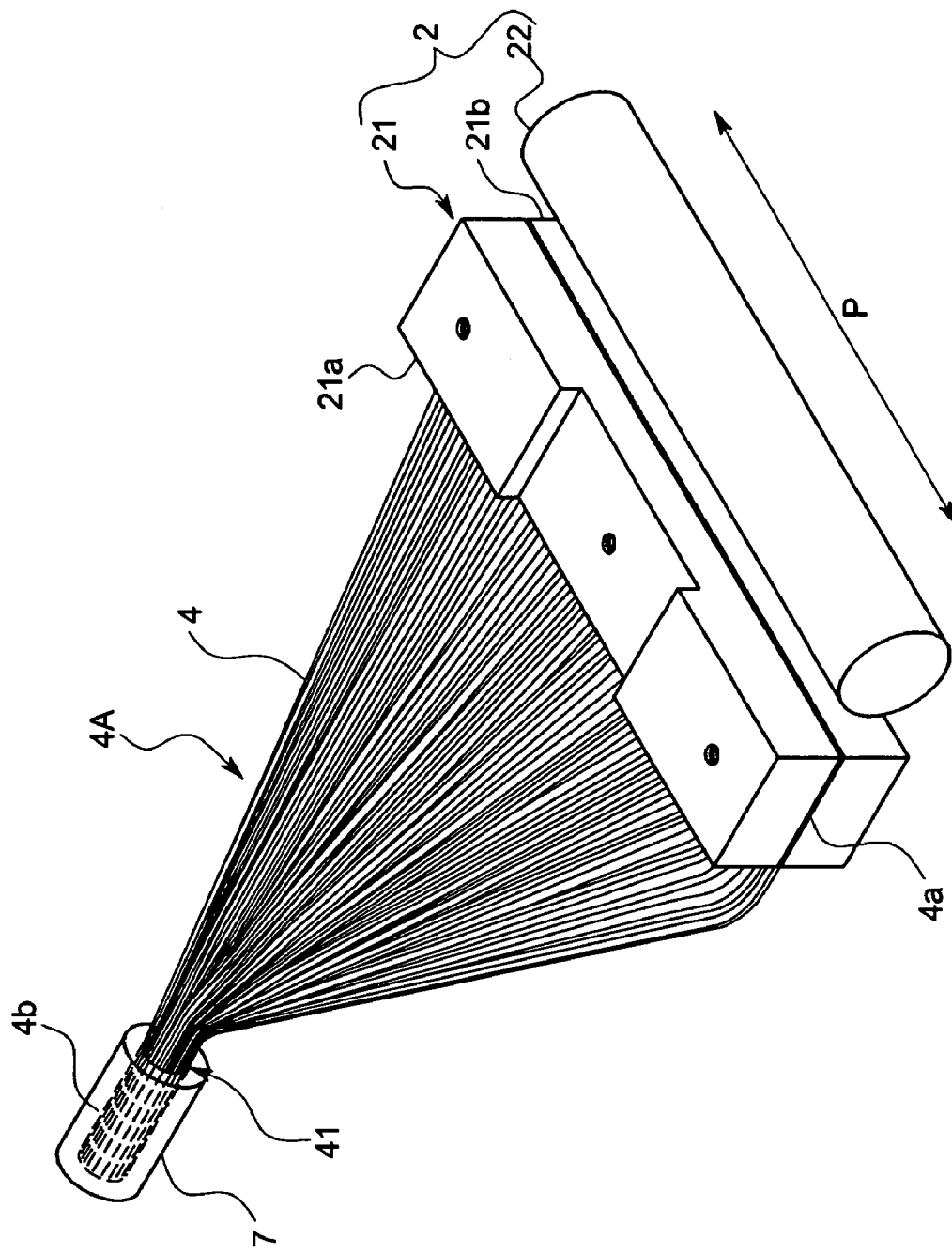
FIG. 5 is a perspective view showing an illustrative embodiment of binding optical fibers in this embodiment.
Figure 6:
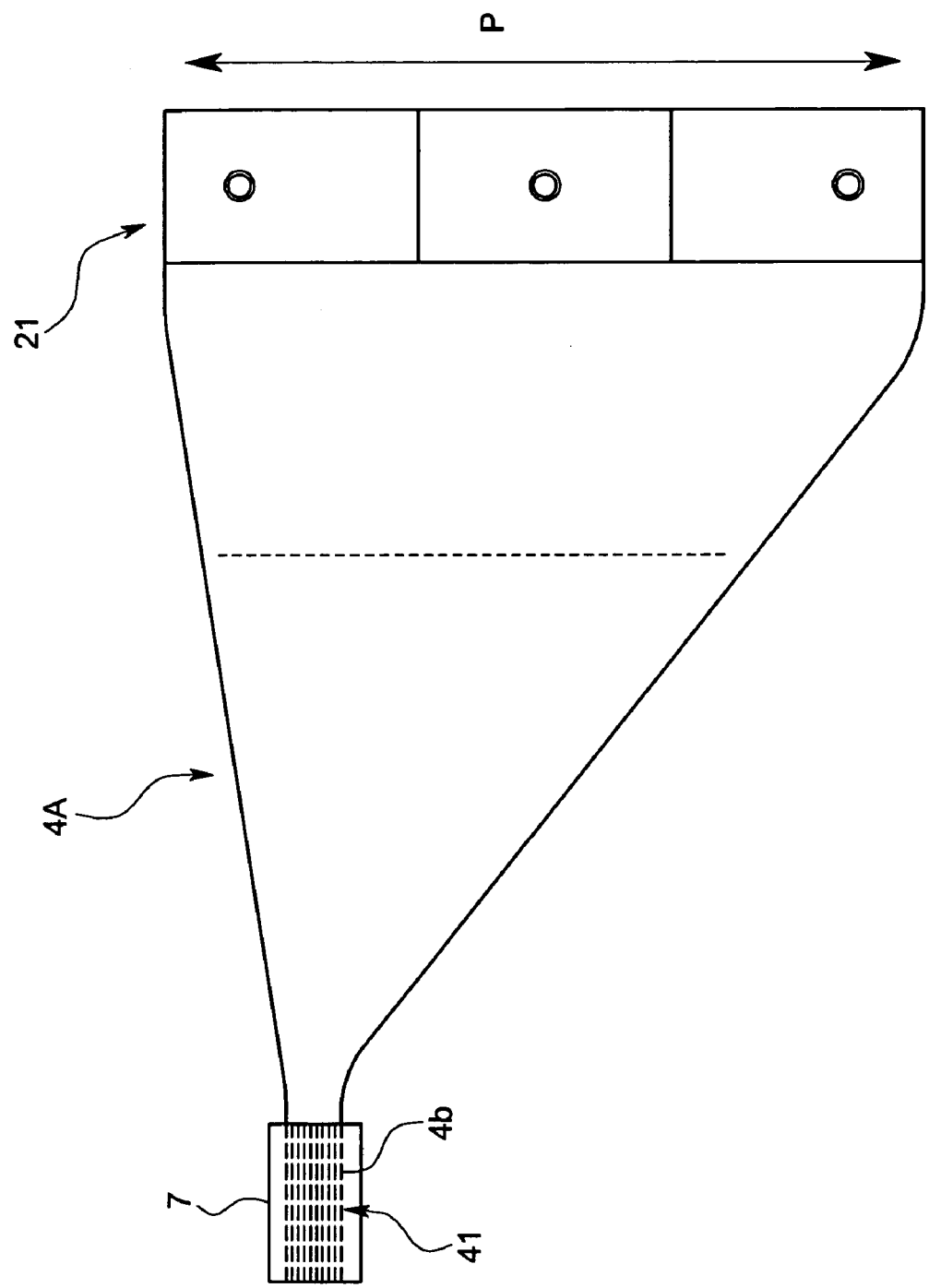
FIG. 6 is a plane view showing the illustrative embodiment of binding the optical fibers in this embodiment.
Figure 7:
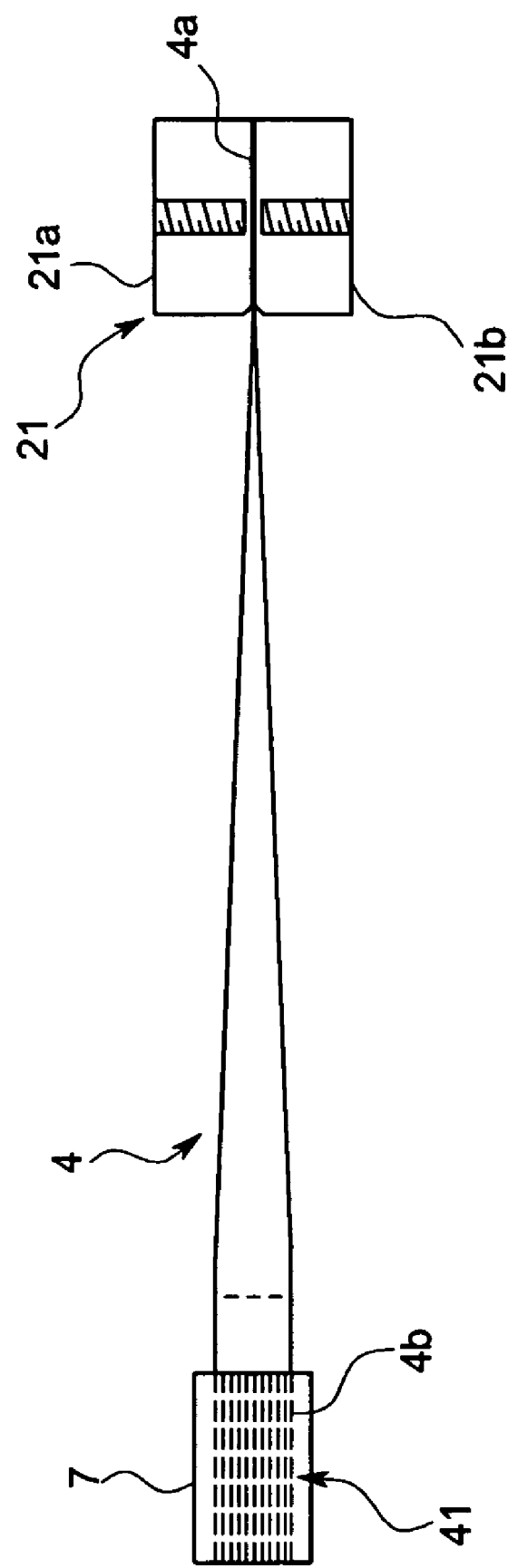
FIG. 7 is a front view showing the illustrative embodiment of binding the optical fibers in this embodiment.

The light irradiating part 21 further comprises, as shown in FIG. 5 through FIG. 7, a pair of plate-shaped pinching plates 21a, 21b. The light irradiating part 21 has an arrangement that each of the light leading out end faces are arranged in several lines without a gap therebetween so as to draw a straight line of a predetermined width (about 0.25 mm through 1 mm) by pinching the light leading out end portions 4a of the optical fibers 4 with the pinching plates 21a, 21b. Each of the rod lenses 22 is a three-dimensional cylindrical column transparent body with a cross-section of a circular form, and arranged so that each center axis of the rod lens 22 locates on an optical axis face T of light irradiated from the light irradiating part 21.

The casing 3 is, as shown in FIG. 1 through FIG. 4, a hollow general cuboid body and a bottom face of the casing 3 is arranged to face to a work W as being an object on which the line light is to be irradiated. Strip-shaped monitoring bores 3a, 3b are arranged to penetrate the top plate 31 and the bottom plate 32 of the casing 3 in order to monitor the work W.

Each of multiple (four in this embodiment) light emitting parts 2 is mounted on the casing 3 in a state of being parallel each other through a fixing member 34 at a position facing to the monitoring bore 3b. Each of the light emitting parts 2 is arranged generally on a straight line viewed from the direction of the line P and the optical axis face T of the line light LL irradiated from each of the light emitting parts 2 is arranged radially viewed from the direction of the line P. More concretely, it is so set that each optical axis face T of the line light LL irradiated from each of the light emitting parts 2 crosses on a predetermined straight line and converges on the predetermined straight line. A measurement of a distance between the light emitting part 2 and its adjacent light emitting part 2 except for the light emitting parts 2 locating side-by-side on the center is so set that each line light LL is arranged to lie side-by-side with generally no gap therebetween and the generally continuous light of a three-dimensional angle is irradiated on the work W.

In addition, light sources 6 of the same number as that of the light emitting parts 2 so as to correspond to each light emitting part 2 are mounted on a side plate 33 of the casing 3 through a bracket 35. Each of the light sources 6 comprises a single power LED (not shown in drawings), a lens mechanism (not shown in drawings) arranged in front of the power LED, and a cylindrical body 61 that accommodates the power LED and the lens mechanism. In this embodiment the light sources 6 are mounted from outside on each of the side plates 33 two by two each of which is arranged side-by-side along a direction of its depth. In order to mount each of the light sources 6, a light source mounting bore 35a that opens toward outside is arranged on the bracket 35. The light source 6 is detachably mounted by fittingly inserting its light emitting end portion into the light source mounting bore 35a by the use of a setscrew B1. The power LED is an LED of a high luminance type that can continuously flow electric current greater than or equal to 200 mA.

The optical fibers 4 are accommodated inside the casing 3 and, as shown in FIG. 5 through FIG. 7, a binding part 41 is formed by thickly binding light introducing end portions 4b of the optical fibers 4 by the use of a cylindrical binding member 7 for each light emitting part 2 and the binding part 41 is mounted on a binding part mounting bore 35b arranged on the bracket 35 from inner side of the binding part mounting bore 35b. More concretely, the binding member 7 is fittingly inserted into the binding part mounting bore 35b and detachably mounted on the binding part mounting bore 35b by the use of a setscrew B2.

One end of the binding part mounting bore 35b opens into an inner side of the bracket 35 and the other end of the binding part mounting bore 35b opens into a bottom of the light source mounting bore 35a. An axis of the binding part mounting bore 35b coincides with an axis of the light source mounting bore 35a. The light source 6 is mounted on the light source mounting bore 35a and the binding member 7 is mounted on the binding part mounting bore 35b. With this arrangement, the light from the light source 6, namely the light from the power LED is converged into a circular form whose diameter is the same as that of the binding part 41 and almost all of the light from the power LED can be introduced into each light introducing end face of the optical fibers 4.

In this embodiment, as shown in FIG. 5 and FIG. 6, each length of all or a part of the optical fibers 4 is made to be different so that the binding part 41 is located to deviate to either one of two directions in a plane view with respect to a center line of the light irradiating part 21. The bound optical fiber band 4A between the binding part 41 and the light emitting part 2 is formed as a sheet form. The optical fiber 4 itself is elastic so that it can be bent; however, it is difficult for the bound optical fiber band 4A as noted above to bend to deviate the binding part 41 of the optical fiber 4 toward the direction of the line P. As a result, with the arrangement of this embodiment wherein the light sources 6 are arranged along a direction of a depth (the direction of the line) P and each light source 6 is located to deviate from the center line of the light emitting part 2 in order to secure downsizing toward the direction of the thickness, this shape that the binding part 41 has been deviated from the center line of the light emitting part 2 before is very effective. In this embodiment, four identical optical fiber bands 4A are formed and mounted two-by-two with its front and back sides turned upside down.

In accordance with thus arranged embodiment, since the light irradiating part 21 is so arranged that distal end portions of optical fibers 4 each of which can be considered as an extremely small point light emitting source are thickly arranged in a line or in several lines and irradiates extremely fine line-shaped light, the irradiated light can be the line light LL that converges into extremely fine line-shaped light even though the irradiated light is gathered by arranging the rod lens 22 whose focal distance is short close to the light irradiating part 21. As a result, it is possible to obtain a lighting device that irradiates light ideally converging in line-shaped light and that is efficient in light focusing, in other words a luminous lighting device, as well as each light irradiating part 2 can be extremely downsized to be an arrangement that occupies little space.

In addition, since the light introducing out end portions 4a are arranged thickly, the line light LL is free from unevenness, thereby enabling to provide the lighting that is high in evenness. Furthermore, it is possible to utilize the rod lens 22 that is inexpensive, thereby to lower costs.

The present claimed invention is not limited to the embodiment.

For example, with the above-mentioned arrangement, in order to prepare several different types of lighting device that irradiates line light whose length differs, it is necessary to change a number of the optical fibers 4 and a length of the pinching plates 21a, 21b for each type of the lighting device In this case, however, it is not possible to standardize basic components such as the optical fibers 4 or the pinching plates 21a, 21b, thereby to diminish a size of a product lot or to increase a labor hour of manufacturing the product.

Figure 8:
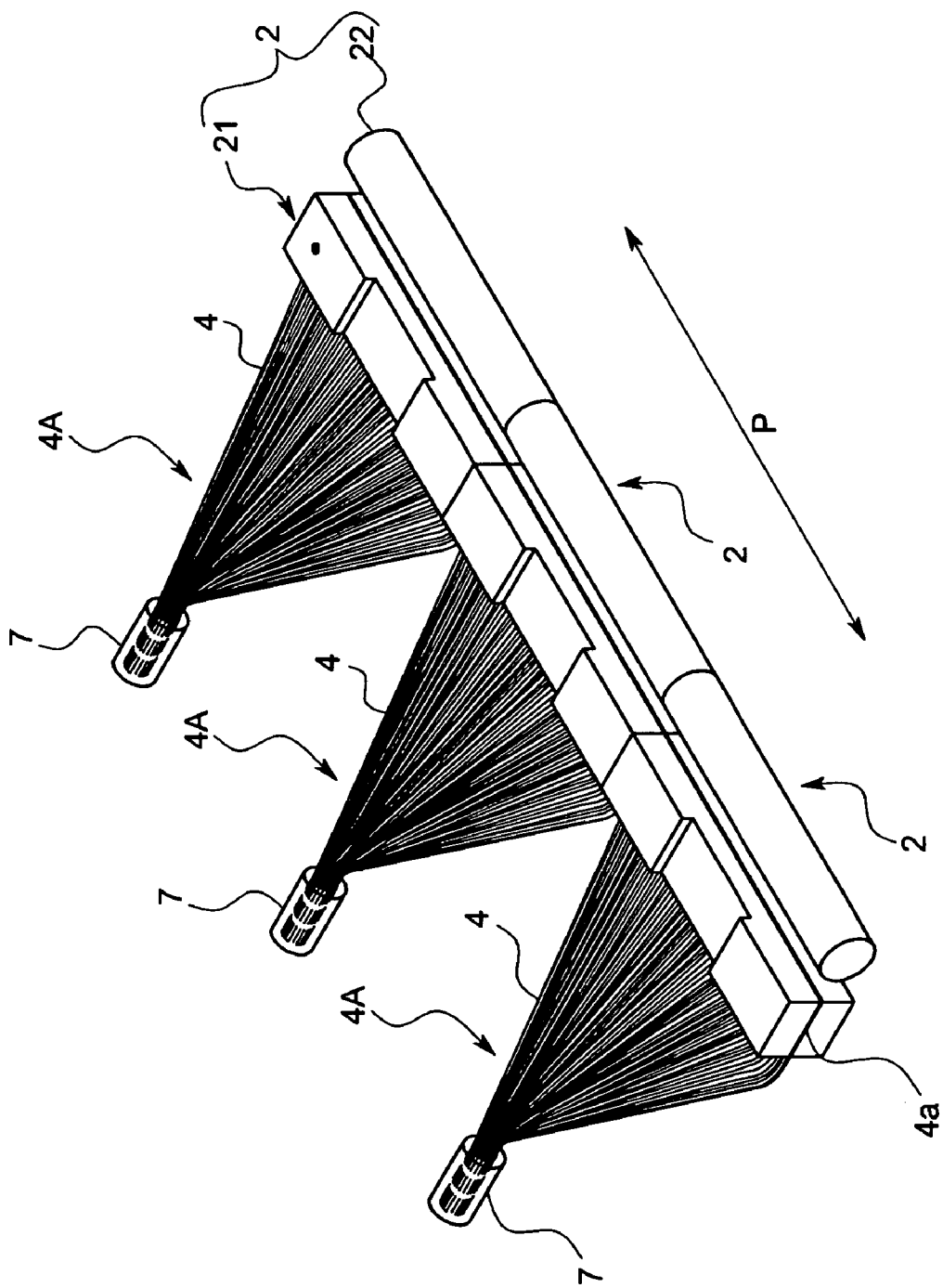
FIG. 8 is a pattern perspective view showing a light emitting part in accordance with another embodiment of the present claimed invention.

In order to solve this problem, this modified embodiment is so arranged that the light emitting part 2 (the light irradiating part 21 and the columnar lens 22) of the identical length and of the identical shape is modularized to be one unit as shown in FIG. 8 and the multiple modularized units are arranged serially along the direction of the line P. Furthermore, a single light source 6 is connected to each light emitting part 2, although not shown in drawings in this embodiment. It is a matter of course that a number of the optical fibers 4 and the shape of the optical fiber band 4A to be connected to each light emitting part 2 are made to be identical.

In accordance with this arrangement, if a number of the serially arranged united light emitting parts 2 is changed, it is possible to prepare several different types of the light irradiation device that irradiates the line light whose length differs and to promote standardization of components of the light irradiation device because the light emitting part 2 as being one of the basic components becomes a single type. As a result of this, a manufacturing cost can be reduced.

Furthermore, since the light intensity can be varied for each light emitting part 2, it is possible to irradiate not only the light of uniform intensity of illumination but also the light of a diversified range. As a result, various effects can be obtained. For example, in case that the lighting device is used for conducting automatic inspection by taking a picture of the work W by a camera (not shown in drawings) through a monitoring bore 3a and by conducting an image processing, an end portion of the image becomes dark due to a lens characteristic of the camera. With a conventional arrangement, this is corrected at a side of an image processing unit. With this arrangement, the S/N ratio is deteriorated due to a process of correction and time to require image processing is necessary. On the contrary, in accordance with the arrangement of this embodiment, if the intensity of illumination at the end portion is made to be stronger than the intensity of illumination at the center portion, the process of correcting image conducted at the side of the image processing unit can be decreased as much as possible. As a result, the S/N ratio can be maintained favorably and high-speed processing can be possible.

On the contrary, with the above-mentioned arrangement, a length of the line light is limited to a value of integral multiplication of the length of the light irradiating part 21. In order to increase variations of the length of the line light, the light irradiating parts 21 of several (two through nine types) different lengths may be arranged serially. However, if too many variations are set in order to be tailored to the length of the light irradiating part 21, an effectiveness of standardizing components is reduced.

In addition, since the columnar lens 22 can be made to be of various lengths only by a cutting process, only the light irradiating part 21 is unitized and the columnar lens 22 is not necessarily unitized. However, if the light emitting part itself 2 is unitized like this embodiment, an effectiveness of modularization can be more remarkable.

In addition to this, there may be various modifications. For example, a half-mirror may be arranged above the monitoring bores 3a, 3b in a slanted posture so that the light is irradiated on the work W also through the monitoring bores 3a, 3b. Furthermore, the monitoring bores 3a, 3b may be blocked with a transparent member such as a glass plate so as to keep inside the casing 3 free of dust.

In addition, a distance between the light irradiating part and the columnar lens may be varied. In accordance with this arrangement, in case of adjusting each optical axis face of the line light irradiated from each light emitting part, convenience is improved as well as a width of the line light irradiated on the work can be varied.

Figure 9:
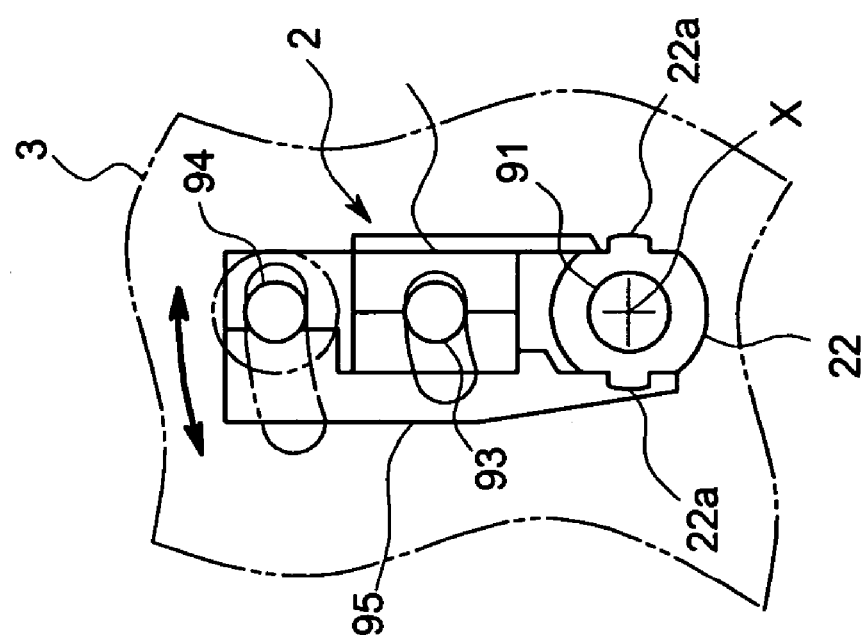
FIG. 9 is a partial side view showing a light emitting part in accordance with further different embodiment of the present claimed invention.
Figure 10:
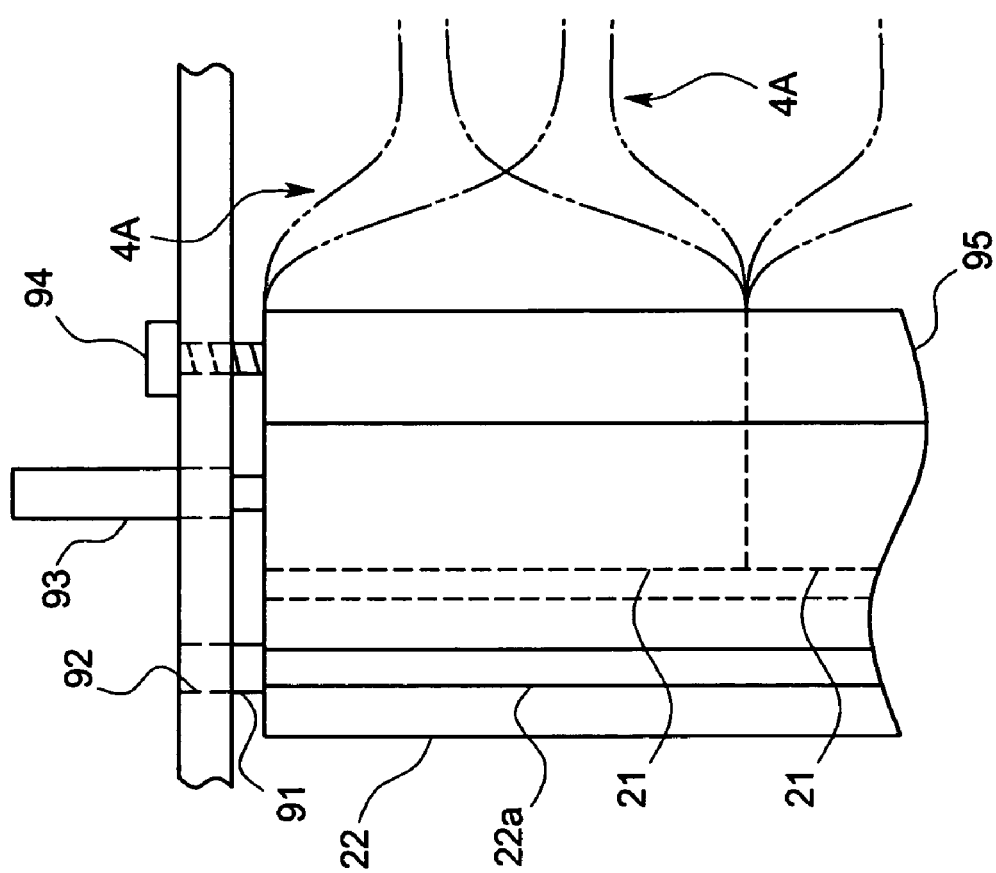
FIG. 10 is a partial plane view showing the light emitting part in accordance with this embodiment.

Alternatively, as shown in FIG. 9 and FIG. 10, the light emitting part 2 may be held by the casing 3 rotatably around a rotational axis that is parallel to the direction of the line so that the light emitting part 2 can be set at an arbitrary angle or an angle of multiple steps within a certain range. In accordance with this arrangement, it is possible to set a position where the light converges on the work by adjusting the angle of each light emitting part according to a distance between the light emitting part and the work.

The rotational center is preferably on the center of the axle of the columnar lens 22. This is because it is possible to restrain interference between each of the light emitting parts 2 due to a rotational movement as much as possible. As a concrete example as a rotational supporting structure of the columnar lens 22, a rotational axis 91 projects from the center of the end face of the columnar lens 22 toward an axial direction (direction of the line) and the rotational axis 91 is supported by a bearing 92 arranged on the casing 3. In addition, in order to change the angle, for example, a handle 93 may project from a rotational center X of the light emitting part 2 or a position deviating from the rotational center X toward the direction of the line so as to change the angle with an operation of the handle 93. Furthermore, in order to fix the angle, for example, a screw 94 may project inward from the casing 3 so as to fix the light emitting part 2 by pushing the end face of the light emitting part 2 with a distal end of the screw 92.

In addition, as mentioned above, in case of arranging the light emitting parts 2 (or the light irradiating parts 21) serially in multiple lines along the direction of the line, as shown in FIG. 9 and FIG. 10, a holding member 95 that holds whole light emitting parts 2 of one line may be arranged and the holding member 95 may be supported by the casing 3 with its rotational angle adjustable.

The columnar lens is not limited to the rod lens, and it may be, for example, a cylindrical lens of half-circle in a cross-sectional view, a Fresnel lens or the like. In addition, as shown in FIG. 9 and FIG. 10, it may be provided with a mount aid part 22a such as a line-shaped convex or a groove extending from a side circumferential portion of the columnar lens 22 that is uninvolved with traveling of the light along the axial direction and the columnar lens 22 may be supported by engaging the holding member 95 with the mount aid part 22a. In accordance with this arrangement, the columnar lens 22 can be held continuously from one end face to the other end face. Then this arrangement makes it possible to hold the columnar lens 22 more securely by restraining bending or distortion of the columnar lens 22 in comparison with an arrangement where only an end portion of the columnar lens 22 is held.

Furthermore, a light homogenization member such as a rod lens that homogenizes the light may be arranged between the light source and the binding part. In accordance with this arrangement, since the intensity of the light introduced into each optical fiber is made to be more equivalent, the unevenness of the intensity of illumination of the line light can be more reduced. As another embodiment to reduce the unevenness of the intensity of illumination of the line light, it is conceived that a diffusion plate such as a lenticular lens is arranged between the light irradiating part and the columnar lens.

In addition, a color of the line light irradiated from each light emitting part may be varied each other or may be changeable.

It is a matter of course that the light source is mounted on an appropriate position such as a top face of the holding body, furthermore the light source is not always mounted on the holding body. For example, the optical fiber may be elongated and the light source may be arranged separately from the holding body. The number of the light source also is not limited to the above-embodiment and may be increased. The light source is not limited to the LEDs.

In addition, the light emitting parts may be arranged, for example, on a circular arc shape viewed from the direction of the line.

DESCRIPTION OF NOTATIONS

1 . . . Line light irradiation device
2 . . . Light emitting parts
21 . . . Light irradiating parts
22 . . . Columnar lens (A rod lens)
21a, 21b . . . Pinching plates
3 . . . Casing
3a, 3b . . . Monitoring bores
4 . . . Optical fibers
41 . . . Binding part
4a . . . optical fiber band
6 . . . Light sources
P . . . Direction of the line
LL . . . Line lights
W . . . Work

The invention claimed is:

1. A line light irradiation device for use in product inspection comprising:
multiple light emitting parts each of which is provided with an optical fiber band and a columnar lens wherein the optical fiber band comprises a light irradiating part formed by arranging light leading out end portions of multiple optical fibers in a straight line or in multiple straight lines and a binding part formed by binding light introducing end portions of the optical fibers and portions of the multiple optical fibers between the light irradiating part and the binding part are formed as a sheet form and the columnar lens is arranged to extend along a direction of the straight line in front of the light irradiating part in pairs, and that irradiate line light that converges into the straight line; and multiple light sources that introduce light into the multiple optical fibers; and a holding body that is arranged to face to an object on which the straight line light is to be irradiated, on which a monitoring bore is arranged to penetrate in order to monitor the object, the holding body holds the light emitting parts so that each optical axis of the line light irradiated from each of the light emitting parts crosses on a predetermined straight line, wherein the light emitting parts are of a same shape and predetermined lengths of the multiple optical fibers of the optical fiber band are made to be different so that the binding part is located to deviate to either one of two directions with respect to a center line of the light irradiating part and two identical optical fiber bands are mounted with their front and back sides turned upside down in the holding body so that the location of each adjacent binding part is different and the multiple light emitting parts are arranged serially along the above mentioned direction of the straight line and the multiple light sources are arranged along the above mentioned direction of the straight line on the holding body and wherein each light emitting part is arranged on the holding body so that the optical axis of the line light irradiated from each light emitting part is arranged radially viewed from the above-mentioned direction of the line.

2. The line light irradiation device described in claim 1, wherein the columnar lens is arranged generally on a straight line viewed from the above-mentioned direction of the line.

3. The line light irradiation device described in claim 1, wherein the light irradiating part further comprises a pair of pinching plates and the pinching plates hold the light leading out end portions of the multiple optical fibers by pinching them between the pair of pinching plates.

4. The line light irradiation device described in claim 1, wherein the light source that introduces light into the optical fibers is a power LED that continuously flows current greater than or equal to 200 mA.

5. The line light irradiation device described in claim 1, wherein a distance between the light irradiating part and the columnar lens is adjustable.

6. The line light irradiation device described in claim 1, wherein the light emitting part is rotatable about a rotational axis that is parallel to the direction of the straight line and the rotational angle at a fixed position.

7. The line light irradiation device described in claim 1, wherein each length of the light emitting part is identical.

8. The line light irradiation device described in claim 1, wherein a light source is arranged for each of the light irradiating parts individually.

9. The line light irradiation device of claim 1, wherein the multiple light emitting parts are modular components that can individually be added or removed to adjust the total operative length of the line light irradiated from the line light irradiation device.

10. A line light irradiation device comprising:
multiple light sources;
multiple light emitting parts, each of which is provided with a light irradiating part where multiple optical fibers with light introducing end portions are bundled into a substantial cylindrical form and aligned with the multiple light sources, and arranged in a line with light leading out end portions of the respective multiple optical fibers for forming a straight line of a predetermined width, and portions of the multiple optical fibers between the light introducing end portions and the light leading out portions are formed as a sheet form, the multiple light emitting parts are arranged serially along the above mentioned direction of the straight line, and each of the multiple light emitting parts is arranged on the holding body so that the optical axis of the line light irradiated from each light emitting part is arranged radially viewed from the above-mentioned direction of the line;

a plurality of columnar lens, each arranged to extend along a direction of a respective line in front of each of the light irradiating parts, and to converge light onto the straight line;

a holding body that is arranged to align with an object on which the line light is to be irradiated, including a monitoring bore arranged to enable a monitoring of the object, the holding body holds the light emitting parts so that each optical axis of light irradiated from each of the light emitting parts crosses at a predetermined straight line, and the multiple light emitting parts are of a same shape, and binding parts that are formed by binding each of the respective light introducing end portions of the optical fibers in the substantially cylindrical form, wherein each length of the optical fibers of all or a part of the optical fibers are different so that the binding part is located to deviate to either one of two directions in a plane view with respect to a center line of the light irradiating part and the respective adjacent binding parts are configured to alternate in deviation to enable adjacent optical fibers to spread into linear arrays that are turned upside down from each other to provide a stacked compact configuration, and the multiple light sources are arranged along the direction of the straight line on the holding body.

11. The line light irradiation device described in claim 10 wherein the light sources are a plurality of light emitting diodes.

12. The line light irradiation device described in claim 10 further includes a cylindrical rod lens aligned with each light emitting end of the optical fiber of each of the multiple light emitting parts to form the line of light on the predetermined surface.

13. The line light irradiation device described in claim 10 where the light source is a plurality of light emitting diodes.

14. The line light irradiation device of claim 10 where the holding body has a rectangular body with a plurality of separate light sources, one light source for each multiple light emitting part, at least two multiple light emitting parts are connected to opposite ends of the rectangular body and the light leading out end portions are positioned to extend parallel to the respective ends of the rectangular body.

15. The line light irradiation device of claim 14 wherein the holding body includes a bracket member mounting at least one of the binding parts, the bracket member is pivotally mounted in the holding body to enable a rotational movement of the mounted binding part to move the line of light of the mounted binding part from a position exterior of the rectangular body.

* * * * *

UNITED STATES PATENT AND TRADEMARK OFFICE
CERTIFICATE OF CORRECTION

PATENT NO. : 7,631,999 B2  Page 1 of 1
APPLICATION NO. : 10/567234
DATED : December 15, 2009
INVENTOR(S) : Yoneda et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 61 days.

Signed and Sealed this

Second Day of November, 2010

David J. Kappos
*Director of the United States Patent and Trademark Office*